(12) United States Patent
Gohno et al.

(10) Patent No.: US 7,187,756 B2
(45) Date of Patent: Mar. 6, 2007

(54) X-RAY CT APPARATUS AND X-RAY TUBE

(75) Inventors: Makoto Gohno, Tokyo (JP); Akira Hagiwara, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/924,111

(22) Filed: Aug. 23, 2004

(65) Prior Publication Data
US 2005/0053189 A1    Mar. 10, 2005

(30) Foreign Application Priority Data
Sep. 5, 2003    (JP)    ............... 2003-313776

(51) Int. Cl.
*H01J 35/10*    (2006.01)
(52) U.S. Cl. .................. 378/124; 378/4; 378/144
(58) Field of Classification Search ............ 378/4, 378/9, 16, 124, 144
See application file for complete search history.

(56) References Cited

U.S. PATENT DOCUMENTS

| | | | |
|---|---|---|---|
| 4,274,005 A | 6/1981 | Yamamura et al. | |
| 4,531,226 A | 7/1985 | Peschmann | |
| 5,268,955 A * | 12/1993 | Burke et al. | ............... 378/135 |
| 5,324,946 A | 6/1994 | Ichihara et al. | |
| 5,485,839 A | 1/1996 | Aida et al. | |
| 5,907,594 A * | 5/1999 | Lai | ............... 378/4 |
| 6,125,167 A * | 9/2000 | Morgan | ............ 378/124 |
| 6,553,097 B2 | 4/2003 | Hansen et al. | |
| 2005/0063514 A1* | 3/2005 | Price et al. | ............ 378/119 |

FOREIGN PATENT DOCUMENTS

JP    06-277208    10/1994

* cited by examiner

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP

(57) ABSTRACT

An X-ray CT apparatus capable of imaging a subject based on X-rays of multiple energy levels while using an ordinary X-ray detector includes an X-ray tube which generates X-rays from multiple focal points of different 3-dimensional positions sequentially on a time-division basis, a plurality of filters which implement the filtering individually for the X-rays generated individually from the focal points, a collimator which equalizes the irradiation range of the X-rays generated individually from the focal points, collection means which collects projection data of multiple views of a subject of imaging for the X-rays generated individually from the focal points, and reconstruction means which reconstructs an image based on the projection data. The anode of the X-ray tube has multiple impingement portions where electrons released by the cathode impinge at multiple positions on the trajectory of electrons sequentially on a time-division basis.

17 Claims, 14 Drawing Sheets

112

114

116

118

X-RAY CT APPARATUS AND X-RAY TUBE

CROSS REFERENCE TO RELATED APPLICATIONS

This application claims the benefit of Japanese Application No. 2003-313776 filed Sep. 5, 2003.

BACKGROUND OF THE INVENTION

The present invention relates to an X-ray CT (Computed Tomography) apparatus and an X-ray tube, and particularly to an X-ray CT apparatus which uses multiple X-rays of different energy levels and to an X-ray tube which is suitable for this X-ray CT apparatus.

An X-ray CT apparatus performs the qualitative tomographic imaging of particular substances by using multiple X-rays of different energy levels. Separation of X-ray energy is based on the use of a multi-layer X-ray detector having inter-layer filters, and X-ray detection signals of different energy levels are obtained from individual layers (refer to patent publication 1 for example).

[Patent publication 1] Japanese Patent Unexamined Publication No. Hei 6(1994)-277208 (FIGS. 1 and 2 on pages 3 and 4)

The above-mentioned X-ray CT apparatus needs a special detector having filters, i.e., multi-layer X-ray detector, and the filters which are interposed between layers need to be large in area enough to cover the whole sensing surface of the X-ray detector.

SUMMARY OF THE INVENTION

It is therefore an object of the present invention to accomplish an X-ray CT apparatus which is capable of performing the imaging based on X-rays of multiple energy levels while using an ordinary X-ray detector. Another object is to accomplish an X-ray tube which is suitable for this X-ray CT apparatus.

(1) At one viewpoint for solving the above-mentioned problem, the present invention resides in an X-ray CT apparatus which is characterized by comprising an X-ray tube which generates X-rays from multiple focal points of different 3-dimensional positions sequentially on a time-division basis, a plurality of filters which implement the filtering individually for the X-rays generated individually from the focal points, a collimator which equalizes the irradiation range of the X-rays generated individually from the focal points, collection means which collects projection data of multiple views of a subject of imaging for the X-rays generated individually from the focal points, and reconstruction means which reconstructs an image based on the projection data.

The X-ray tube is an X-ray tube having an anode and a cathode which confront each other and generating X-rays from focal points on the anode where electrons from the cathode impinge, wherein for the generation of X-rays sequentially on a time-division basis, it is desirable for the anode to have multiple impingement portions where electrons released by the cathode impinge at multiple positions on the trajectory of electrons sequentially on a time-division basis.

(2) At another viewpoint for solving the above-mentioned problem, the present invention resides in an X-ray tube which is characterized by having an anode and a cathode which confront each other and generating X-rays from focal points on the anode where electrons from the cathode impinge, wherein the anode has multiple impingement portions where electrons released by said cathode impinge at multiple positions on the trajectory of electrons sequentially on a time-division basis.

The anode is a plurality of rotary plates which are parallel to each other and share a rotation shaft which is parallel to the trajectory of electrons, wherein at least rotary plates located from the position nearest to the cathode up to the position immediately before the position farthest from the cathode each have large-radius sections with a radius larger than the distance from the rotation center to the trajectory of electrons and small-radius sections with a radius smaller than the distance from the rotation center to the trajectory of electrons by being formed alternately along the rotational direction, and for the formation of focal points at multiple positions on the trajectory of electrons, it is desirable for the rotary plates to have the large-radius sections which do not overlap in the direction parallel to the trajectory of electron beam. For the formation of focal points at two positions on the trajectory of electrons, it is desirable for the multiple rotary plates to be two rotary plates.

The anode is two rotary plates which are parallel to each other and share a rotation shaft which is parallel to the trajectory of electrons released by the cathode, wherein the rotary plates have X-ray generation sections and X-ray non-generation sections laid out on the surfaces of opposite sides alternately along the rotational direction such that the X-ray generation sections on the surfaces of opposite sides do not overlap in the direction parallel to the rotation shaft, and for the formation of focal points at two positions on the trajectory of electrons, it is desirable for the cathode to generate electrons which impinge on to the surfaces of opposite sides of the two rotary plates.

For the formation of multiple focal points on each of multiple trajectories of electrons, it is desirable for the anode and cathode to be in multiple pairs. For the formation of multiple focal points on each of two trajectories of electrons, it is desirable for the pairs to be two pairs. For the formation of multiple focal points having a same distance to the X-ray sensing surface, it is desirable for the focal points to be all located on the same horizontal plane. For the formation of multiple focal points having different distances to the X-ray sensing surface, it is desirable for the focal points to be all located on a same plane which is aslant against the horizontal plane.

According to the invention at the one viewpoint, the X-ray CT apparatus comprises an X-ray tube which generates X-rays from multiple focal points of different 3-dimensional positions sequentially on a time-division basis, a plurality of filters which implement the filtering individually for the X-rays generated individually from the focal points, a collimator which equalizes the irradiation range of the X-rays generated individually from the focal points, collection means which collects projection data of multiple views of a subject of imaging for the X-rays generated individually from the focal points, and reconstruction means which reconstructs an image based on the projection data, whereby it is possible to perform the imaging based on X-rays of multiple energy levels while using an ordinary X-ray detector.

According to the invention at the other viewpoint, the anode of X-ray tube has multiple impingement portions where electrons released by the cathode impinge at multiple positions on the trajectory of electrons sequentially on a time-division basis, whereby it is possible to accomplish an X-ray tube which generates X-rays from multiple focal points of different 3-dimensional positions sequentially on a time-division basis, i.e., an X-ray tube which is suitable for imaging based on X-rays of multiple energy levels.

Further objects and advantages of the present invention will be apparent from the following description of the preferred embodiments of the invention as illustrated in the accompanying drawings.

DETAILED DESCRIPTION OF THE INVENTION

Figure 1:
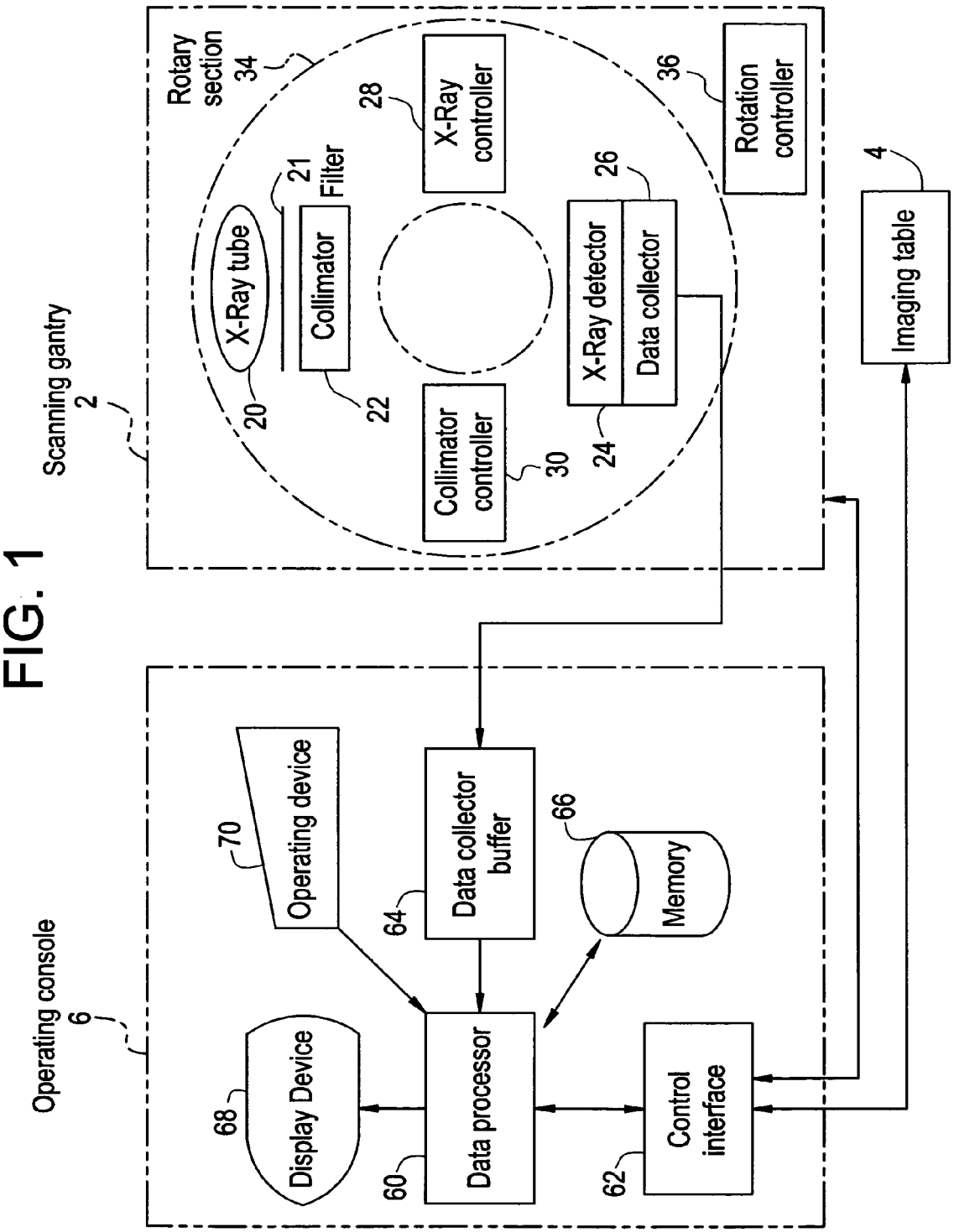
FIG. 1 is a block diagram of the X-ray CT apparatus.

The best mode for carrying out the invention will be explained with reference to the drawings. FIG. 1 shows a block diagram of an X-ray CT apparatus. This apparatus is an example of the best mode for carrying out the invention. The arrangement of this apparatus reveals an example of the best mode for carrying out this invention which pertains to an X-ray CT apparatus.

As shown FIG. 1, the apparatus includes a scanning gantry 2, an imaging table 4, and an operation console 6. The scanning gantry 2 has an X-ray tube 20. The X-ray tube 20 emits X-rays (not shown), which are filtered by a filter 21, collimated by a collimator 22 to become a fan-shaped X-ray beam, i.e., fan beam X-rays, and cast on to an X-ray detector 24. The X-ray detector 24 has multiple sensing elements which are arrayed to match with the fan-out of X-ray beam. The structure of the X-ray detector 24 will be explained in detail later. A subject of imaging placed on the imaging table 4 is carried into the space between the X-ray tube 20 and the X-ray detector 24.

The X-ray tube 20 has multiple focal points, from which X-rays are generated individually, as will be explained in detail later. The filter 21 includes multiple filters in correspondence to the multiple X-rays, and they filter the corresponding X-rays. The collimator 22 includes multiple collimators in correspondence to the multiple X-rays, and they collimate the corresponding X-rays.

The filter 21 is an example of the filter of this invention. The collimator 22 is an example of the collimator of this invention. The X-ray tube 20, filter 21, collimator 22, and X-ray detector 24 in unison constitute X-ray irradiation/detection equipment. The X-ray irradiation/detection equipment will be explained in detail later.

The X-ray detector 24 is connected to a data collector 26. The data collector 26 collects as digital data the detection signals of the individual sensing elements of the X-ray detector 24. The portion of apparatus including the X-ray detector 24 and data collector 26 is an example of collection means of this invention. The detection signals of the sensing elements become a signal which indicates the X-ray projection image of the subject. The signal will be called projection data, or simply data.

Irradiation of X-rays from the X-ray tube 20 is controlled by an X-ray controller 28. The figure does not show the connection between the X-ray tube 20 and the X-ray controller 28. The collimator 22 is controlled by a collimator controller 30. The figure does not show the connection between the collimator 22 and the collimator controller 30.

The above-mentioned equipment from the X-ray tube 20 up to the collimator controller 30 are mounted on a rotor 34 of the scanning gantry 2. The rotor 34 has its rotation controlled by a rotation controller 36. The figure does not show the connection between the rotor 34 and the rotation controller 36.

The operation console 6 has a data processor 60. The data processor 60 is a computer or the like for example. The data processor 60 is connected to a control interface 62. The control interface 62 is connected to the scanning gantry 2 and imaging table 4. The data processor 60 controls the scanning gantry 2 and imaging table 4 through the control interface 62.

The data collector 26, X-ray controller 28, collimator controller 30 and rotation controller 36 in the scanning gantry 2 are controlled through the control interface 62. The figure does not show the individual connection between these devices and the control interface 62.

The data processor 60 is connected to a data collector buffer 64. The data collector buffer 64 is connected to the data collector 26 in the scanning gantry 2. Data collected by the data collector 26 is put in to the data processor 60 via the data collector buffer 64.

The data processor 60 is connected to a memory 66. The memory 66 stores projection image data which has been put in to the data processor 60 via the data collector buffer 64 and control interface 62. The memory 66 also stores programs for the data processor 60. The data processor 60 runs the programs, causing the apparatus to operate.

The data processor 60 implements the image reconstruction by use of the projection image data which has been collected in the memory 66 by via the data collector buffer 64. The data processor 60 is an example of reconstruction means of this invention. Image reconstruction is based on the filtered back projection scheme or the like for example.

The data processor 60 is connected to a display device 68 and operation device 70. The display device 68 is a graphic display device or the like. The operation device 70 is a keyboard or the like equipped with a pointing device.

The display device 68 displays the reconstructed image put out from the data processor 60 and other information. The operation device 70 is operated by the user to enter various commands and information to the data processor 60. The user uses the display device 68 and operation device 70 to operate the apparatus in interactive manner.

Figure 2:
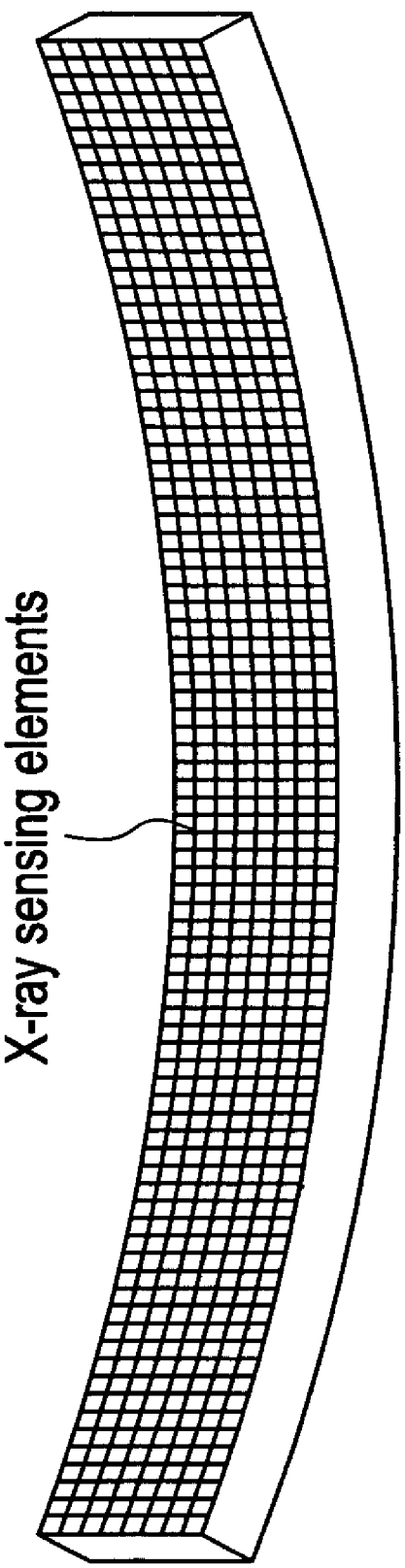
FIG. 2 is a diagram showing the arrangement of the X-ray detector.

FIG. 2 shows schematically the structure of the X-ray detector 24. The X-ray detector 24 is a multi-channel X-ray detector formed of a 2-dimensional array of X-ray sensing elements 24($ik$). The X-ray sensing elements 24($ik$) make an arching X-ray sensing surface of a cylindrical concave surface shape as a whole.

The elements have channel numbers i ranging from 1 to 1000 and column numbers k ranging from 1 to 32. X-ray sensing elements 24($ik$) of a same column number k form a sensing element column. The number of sensing element columns of the X-ray detector 24 is not confined to 32, but it can be arbitrary inclusive of unitary.

The X-ray sensing elements 24($ik$) are each formed of a scintillator diode and a photodiode in combination. The elements are not confined to this type, but they can be semiconductor X-ray sensing elements based on cadmium tellurium (CdTe) or the like, or X-ray sensing elements of the type of ionization chamber using xenon (Xe) gas.

Figure 3A:
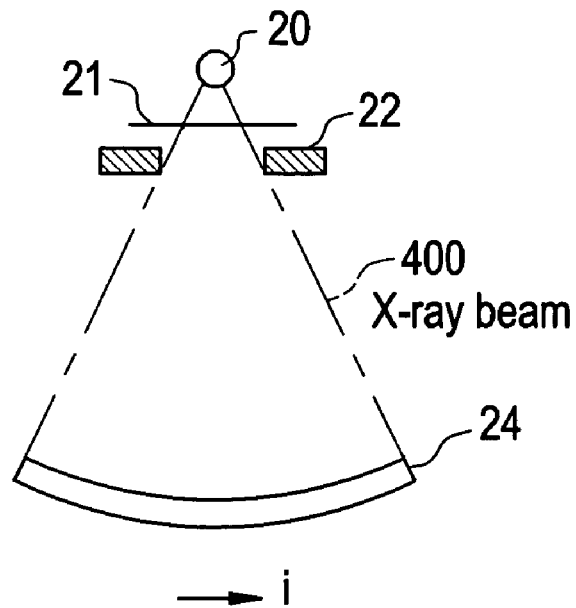
FIG. 3(a) and FIG. 3(b) are diagrams showing the arrangement of the X-ray irradiation/detection equipment.
Figure 3B:
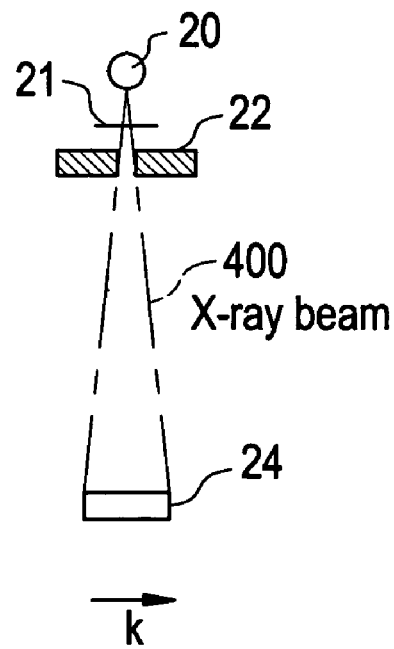

FIG. 3($a$) and FIG. 3($b$) show the relation among the X-ray tube 20, collimator 22 and X-ray detector 24 of the X-ray irradiation/detection equipment. FIG. 3($a$) is a front view of the scanning gantry 2, and FIG. 3($b$) is a side view of it. The X-rays emitted by the X-ray tube 20 are shaped into a fan-out X-ray beam 400 by the collimator 22 and cast on to the X-ray detector 24.

FIG. 3($a$) shows the fan-out in one direction of the X-ray beam 400. This direction will be called the width direction. The width direction of the X-ray beam 400 coincides with the channel aligning direction of the X-ray detector 24. FIG. 3($b$) is the fan-out in another direction of the X-ray beam 400. This direction will be called the thickness direction of the X-ray beam 400. The thickness direction of the X-ray beam 400 coincides with the traversal direction of the sensing element column of the X-ray detector 24. The two fan-out directions of the X-ray beam 400 are orthogonal to each other.

Figure 4:
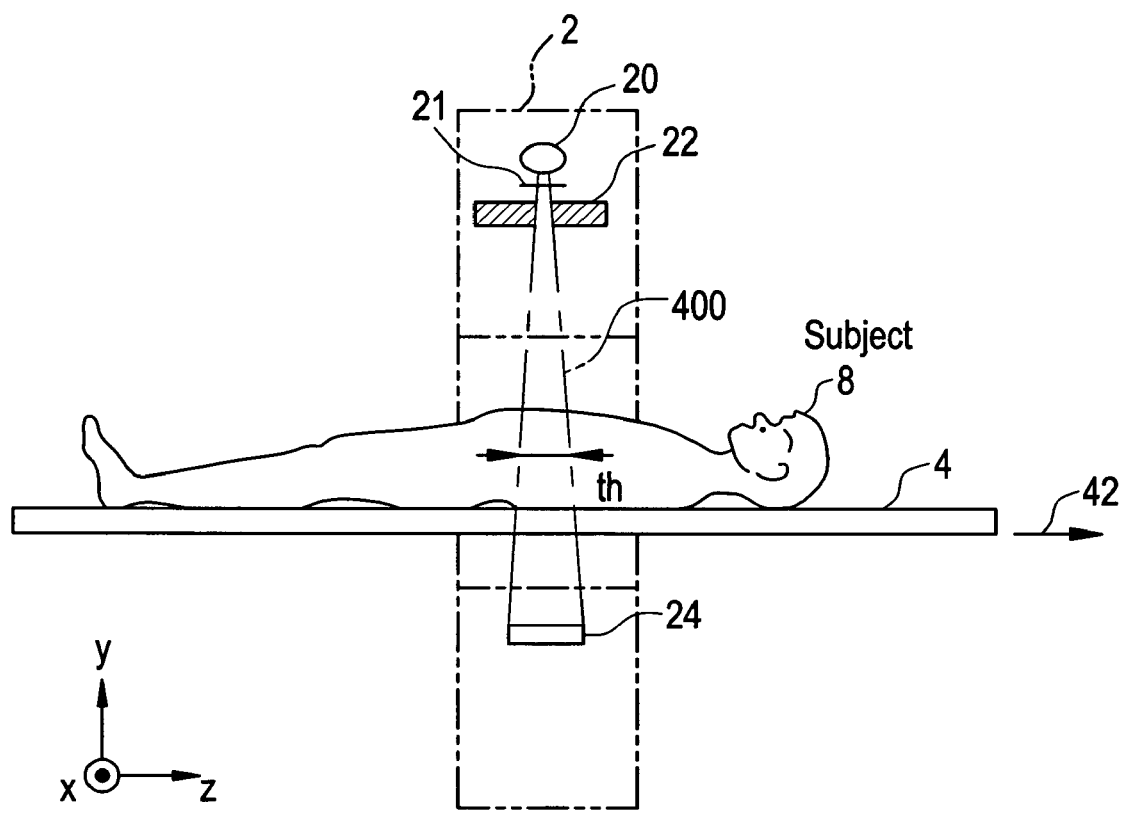
FIG. 4 is a diagram showing the relation between the X-ray irradiation/detection equipment and the subject of imaging.

FIG. 4 is a diagram showing an embodiment of a relationship between the X-ray irradiation/detection equipment and subject 8. With the body axis being set crisscross against the fan-out plane of the X-ray beam 400, the subject 8 placed on the imaging table 4 is carried into the X-ray irradiation space. The scanning gantry 2 has a cylindrical structure to accommodate the X-ray irradiation/detection equipment.

The X-ray irradiation space is formed in the interior of the cylindrical structure of the scanning gantry 2. A sliced image of the subject 8 produced by the X-ray beam 400 is projected on to the X-ray detector 24. The X-ray detector 24 detects the X-rays coming through the subject 8. The thickness "th" of the X-ray beam 400 irradiated to the subject 8 is adjusted in terms of the degree of opening of aperture of the collimator 22.

The imaging table 4 is moved continuously along the body axis of the subject 8 as indicated by the arrow 42 simultaneously to the rotation of the X-ray irradiation/detection equipment so that the X-ray irradiation/detection equipment turns relative to the subject 8 along a spiral trajectory which encloses the subject 8, thereby performing the so-called helical scanning. Rotating the X-ray irradiation/detection equipment, with the imaging table 4 being held stationary, performs the axial scanning. The direction of rotation axis of scanning is defined to be the z direction, the direction of a line which connects between the rotation center and the X-ray tube 20 is defined to be the y direction, and the direction orthogonal to the y direction is defined to be the x direction. These directions establish a revolving coordinate system xyz.

Projection image data of multiple (e.g., around 1000) views is collected in one scanning rotation. Collection of projection image data is implemented by a system of the X-ray detector 24, data collector 26 and data collector buffer 64. Projection image data will also be called scanning data in the following explanation. Projection image data of each view will also be called view data.

Figure 5:
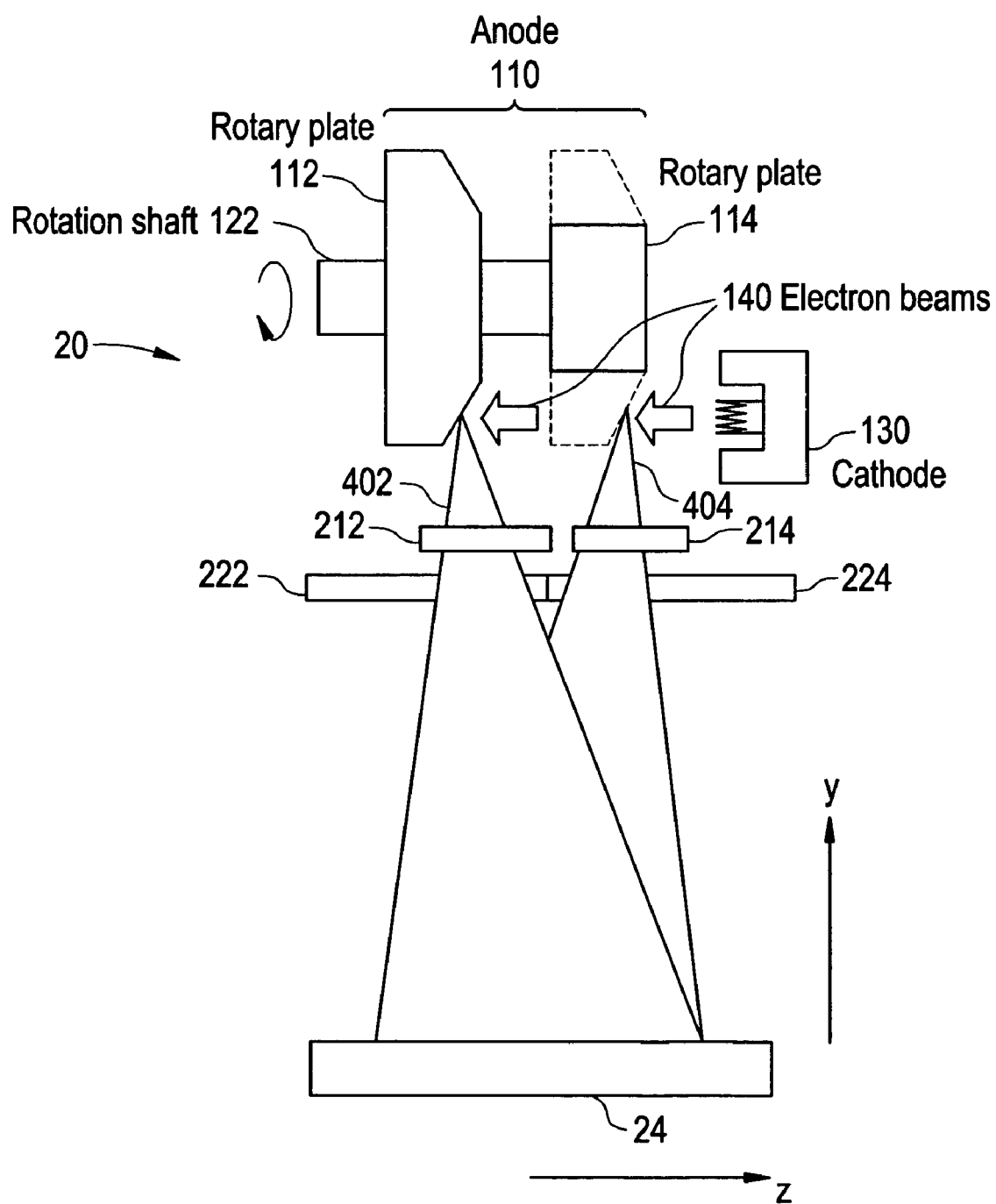
FIG. 5 is a diagram showing the arrangement of the X-ray irradiation/detection equipment.

The X-ray irradiation/detection equipment will be explained. FIG. 5 shows schematically the structure of the X-ray irradiation/detection equipment. The X-ray tube 20 has an anode 110 and a cathode 130 as shown in the figure. A high voltage is applied between the anode 110 and the cathode 130. Electrons accelerated by the high voltage form an electron beam 140, which radiates from the cathode 130 toward the anode 110. The anode 110 and cathode 130 are encased in a vacuum tube which is not shown. The X-ray tube 20 is an example of the best mode for carrying out this invention. The structure of this X-ray tube 20 reveals an example of the best mode for carrying out this invention which pertains to an X-ray tube.

Figure 6:
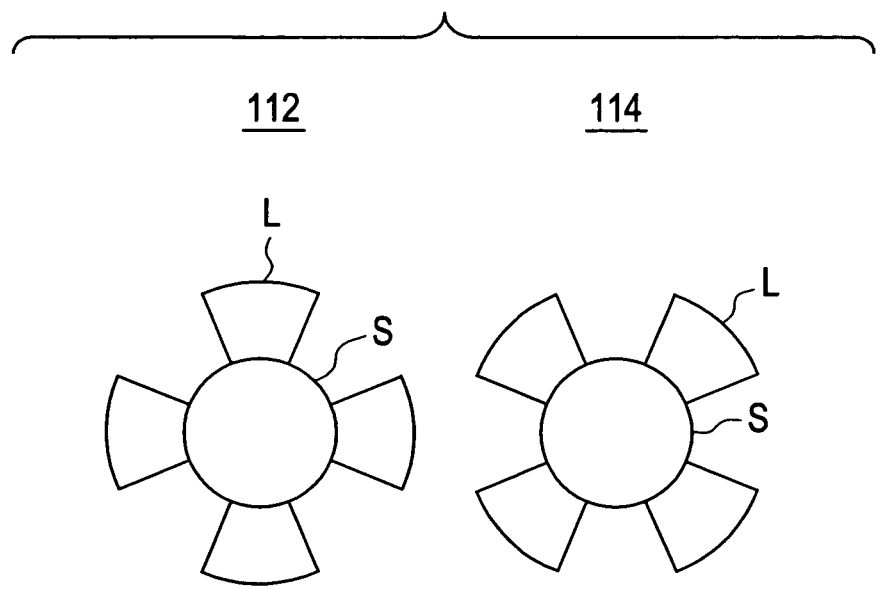
FIG. 6 is a diagram showing the arrangement of the rotary plates of the anode.

The anode 110 has two rotary plates 112 and 114 which are parallel to each other. The rotary plates 112 and 114 share a rotation shaft 122. The rotation shaft 122 and the electron beam are in the z direction. FIG. 6 shows the shape of the rotary plates 112 and 114 seen from the cathode 130. The rotary plates 112 and 114 each have large-radius sections L and small-radius sections S as shown in the figure. The large-radius sections L and small-radius sections S are formed alternately along the rotational direction.

The large-radius sections L have a radius larger than the distance from the rotation center to the trajectory of electrons, and the small-radius sections have a radius smaller than the distance from the rotation center to the trajectory of electrons. The rotary plates 112 and 114 are related in arrangement such that their large-radius sections L and small-radius sections S interleave when seen from the cathode 130. Accordingly, the large-radius sections L of the rotary plates 112 and 114 do not overlap in the direction of electron beam. Consequently, electrons impinge on to the rotary plates 112 and 114 alternately as the anode 110 rotates, and X-rays 402 and 404 are generated alternately from the rotary plates 112 and 114, with the impingement positions thereof being focal points. The rotary plate 112 may be a circular disc having the large radius L in its entirety. Even in this case, it is possible to generate X-rays 402 and 404 alternately due to the location of the rotary plate 112 behind the rotary plate 114 when seen from the cathode 130.

Based on this structure, the X-rays 402 and 404 are generated from two focal points of different positions on the trajectory of electrons alternately on a time-division basis. The two focal points differ in their 3-dimensional positions in the revolving coordinate system. The two X-rays have their generation timing determined mechanically based on the positions of the large-radius sections of the rotary plates 112 and 114, facilitating X-ray generation control. The capability of quick switching of the two X-rays results in X-rays with superior pulse characteristics.

The X-rays 402 are filtered by the filter 212, collimated by the collimator 222, and applied to the X-ray detector 24. The X-rays 404 are filtered by the filter 214, collimated by the collimator 224, and applied to the X-ray detector 24. The collimators 222 and 224 implement the collimation such that the X-rays 402 and 404 are cast on to the same sensing surface of the X-ray detector 24. The filters 212 and 214 merely need to have areas enough to cover the apertures of the collimators 222 and 224, instead of having areas to cover the whole sensing surface of the X-ray detector 24.

The filters 212 and 214 have different energy selecting characteristics. Consequently, the X-rays 402 and 404 become to have different energy levels after the rendition of filtering. Due to the irradiation of two kinds of X-rays of different energy levels taking place alternately on a time-division basis, the X-ray detector 24 produces detection signals which correspond to the two kinds of X-rays alternately on a time-division basis. Accordingly, the X-ray detector 24 can be an ordinary X-ray detector instead of the need of individual detectors for both kinds of X-rays. The X-rays 402 and 404 may have their energy levels varied based on the application voltages of individual rotary plates, in place of the use or in addition to the use of the filters 212 and 214. This affair is also relevant to the following explanation.

Figure 7:
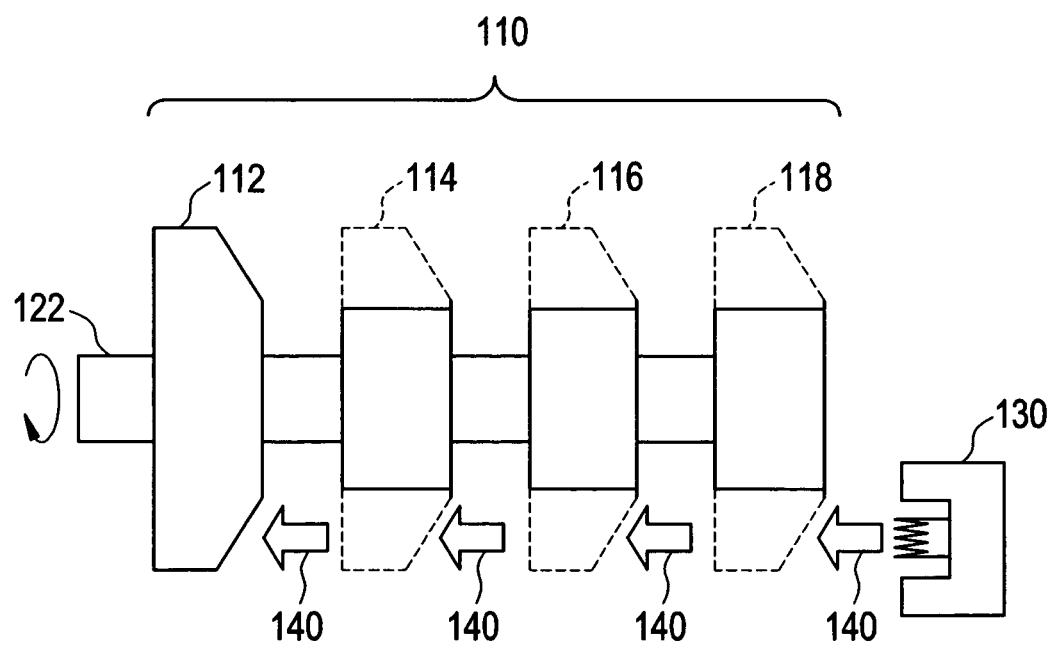
FIG. 7 is a diagram showing the arrangement of the rotary plates of the anode.
Figure 8:
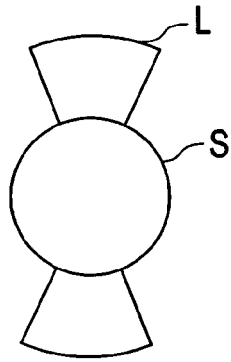
FIG. 8 is a diagram showing the arrangement of the rotary plates of the anode.
Figure 8:
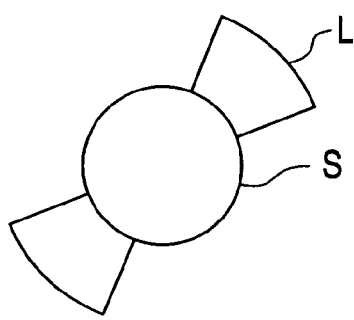
Figure 8:
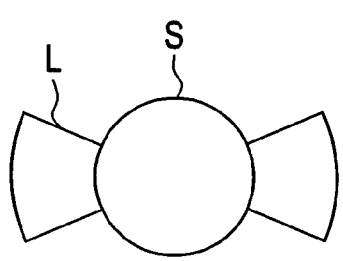
Figure 8:
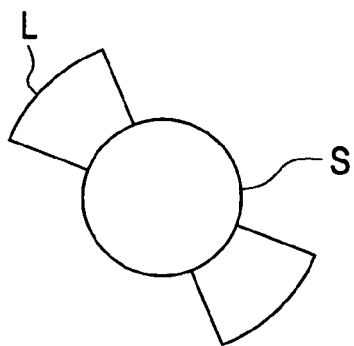

The anode 110 may be designed to have more than two rotary plates. FIG. 7 shows schematically an example of anode having four rotary plates. The anode 110 has rotary plates 112,114,116 and 118 as shown in the figure. The rotary plates 112,114,116 and 118 share a rotation shaft 122. The rotary plates 112,114,116 and 118 have a shape seen from the cathode 130 as shown in FIG. 8. Each of the rotary plates 112,114, 116 and 118 has large-radius sections L and small-radius sections S, with the plates being arranged such that their large-radius sections do not overlap in the direction of electron beam, as shown in the figure.

Consequently, electrons impinge on to the rotary plates 112,114,116 and 118 in turn as the anode 110 rotates, and X-rays are generated from the positions of impingement as focal points sequentially on a time-division basis. The rotary plate 112 may be a circular disc having the large-radius section L in its entirety. Also in this case, it is possible to generate X-rays in turn on a time-division basis due to the location of the rotary plate 112 farthest from the cathode 130.

In this manner, X-rays are generated from four focal points of different positions on the trajectory of electrons sequentially on a time-division basis. The four X-rays have their generation timing determined mechanically based on the positions of the large-radius sections of the rotary plates 112,114,116 and 118, facilitating X-ray generation control. The capability of quick switching of the four X-rays results in X-rays with superior pulse characteristics. Filtering these X-rays separately with four filters having different energy selecting characteristics produces four X-ray of different energy levels.

Figure 9:
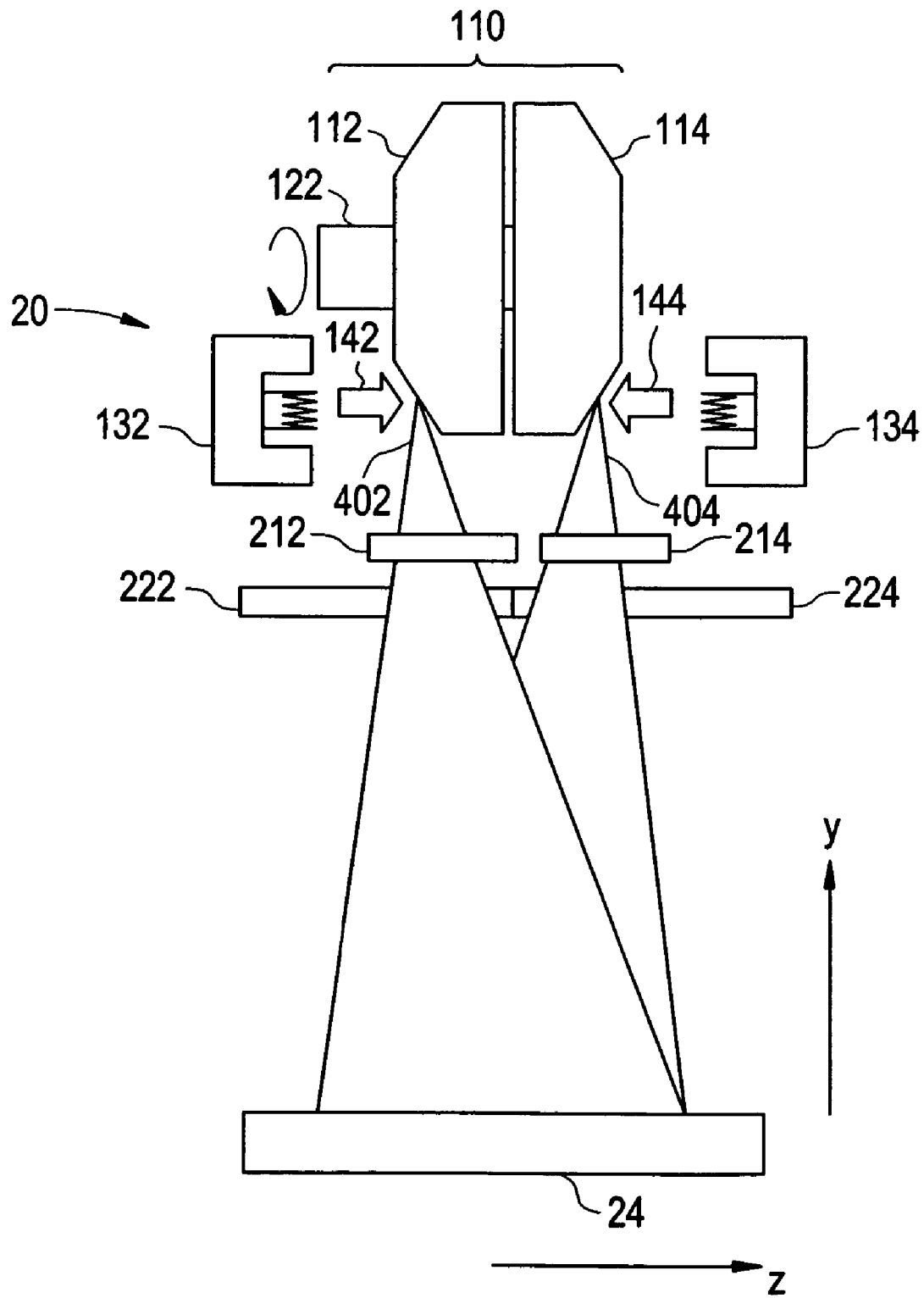
FIG. 9 is a diagram showing the arrangement of the X-ray irradiation/detection equipment.

In case only two kinds of X-rays of different energy levels are necessary, the anode and cathode may be arranged as shown in FIG. 9. The anode 110 has two parallel rotary plates 112 and 114 as shown in the figure. These rotary plates 112 and 114 share a rotation shaft 122. The shaft 122 extends in the z direction. The rotary plates 112 and 114 are accompanied by two cathodes 132 and 134 correspondingly. The rotary plates 112 and 114 are situated back-to-back, and the cathodes 132 and 134 confront the rotary plates 112 and 114 on their back sides. The rotary plate 112 which confronts the cathode 132 radiates an electron beam 142, and the rotary plate 114 which confronts the cathode 134 radiates another electron beam 144. The rotary plates 112 and 114 may be unified to be one rotary plate.

Figure 10:
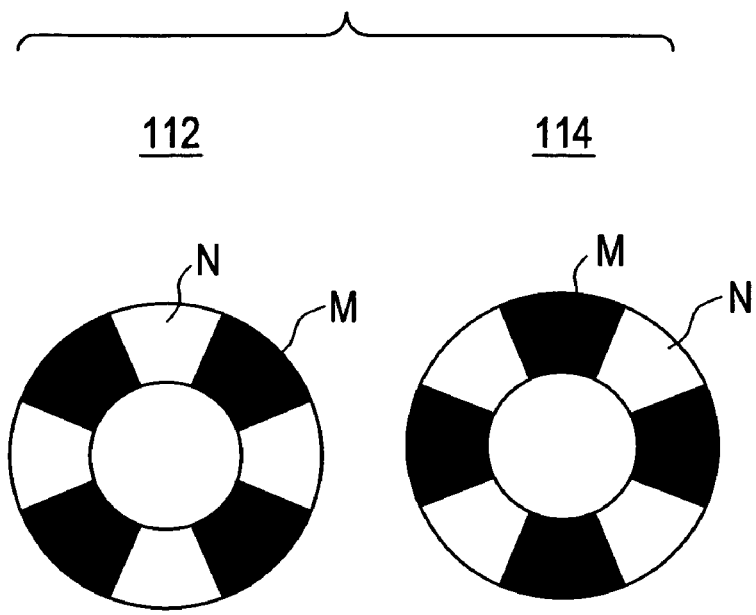
FIG. 10 is a diagram showing the arrangement of the rotary plates of the anode.

FIG. 10 shows the shape of the rotary plates 112 and 114 seen from the cathodes 132 and 134. The rotary plates 112 and 114 each have X-ray generation sections M and X-ray non-generation sections N as shown in the figure. The X-ray generation sections M and X-ray non-generation sections N are formed alternately along the rotational direction. There is put to the X-ray generation sections M a material which generates X-rays in the presence of electron impingement, while there is put to the X-ray non-generation sections N a material which substantially does not generate X-rays in the presence of electron impingement.

The rotary plates 112 and 114 are related in arrangement such that their X-ray generation sections M and X-ray non-generation sections N interleave when seen from the cathodes 132 and 134. Accordingly, the X-ray generation sections M of the rotary plates 112 and 114 do not overlap in the direction of electron beam. Consequently, electrons impinge on to the X-ray generation sections M of the rotary plates 112 and 114 alternately as the anode 110 rotates, and X-rays 402 and 404 are generated alternately from the rotary plates 112 and 114, with the impingement positions thereof being focal points.

In this manner, X-rays are generated from two focal points of different positions on the trajectory of electrons alternately on a time-division basis. The two X-rays have their generation timing determined mechanically based on the positions of the X-ray generation sections M of the rotary plates 112 and 114, facilitating X-ray generation control. The capability of quick switching of the two X-rays results in X-rays with superior pulse characteristics.

Figure 11:
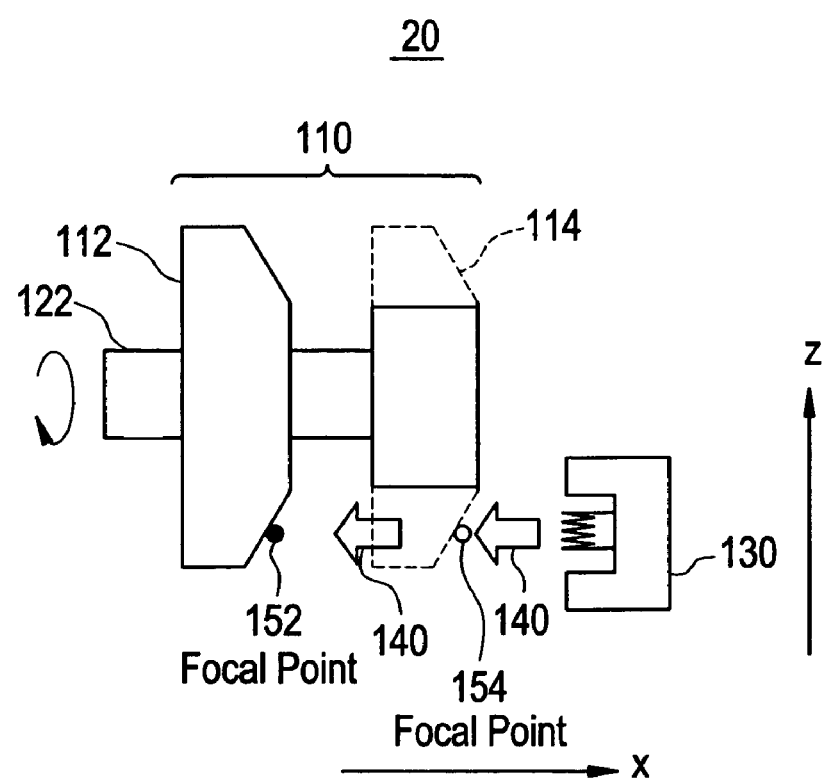
FIG. 11 is a diagram showing the location of the multiple focal points.

The focal points may be located along the x direction, instead of the z direction described above. FIG. 11 shows an example of this case. The rotation shaft 122 and electron beam 140 have their direction set to be along the x direction as shown in the figure. Consequently, there is accomplished an X-ray tube 20 which generates X-rays from the two focal points 152 and 154 located along the x direction alternately on a time-division basis.

In case the X-ray tube 20 has four anodes as shown in FIG. 7, there is accomplished an X-ray tube which generates X-rays from the four focal points located along the x direction sequentially on a time-division basis. In the case of provision of two anodes and corresponding cathodes which are situated back-to-back as shown in FIG. 9, with the rotation shaft 122 and electron beam 140 having their direction set to be along the x direction, and there is accomplished an X-ray tube 20 which generates X-rays from the two focal points located along the x direction alternately on a time-division basis.

Figure 12:
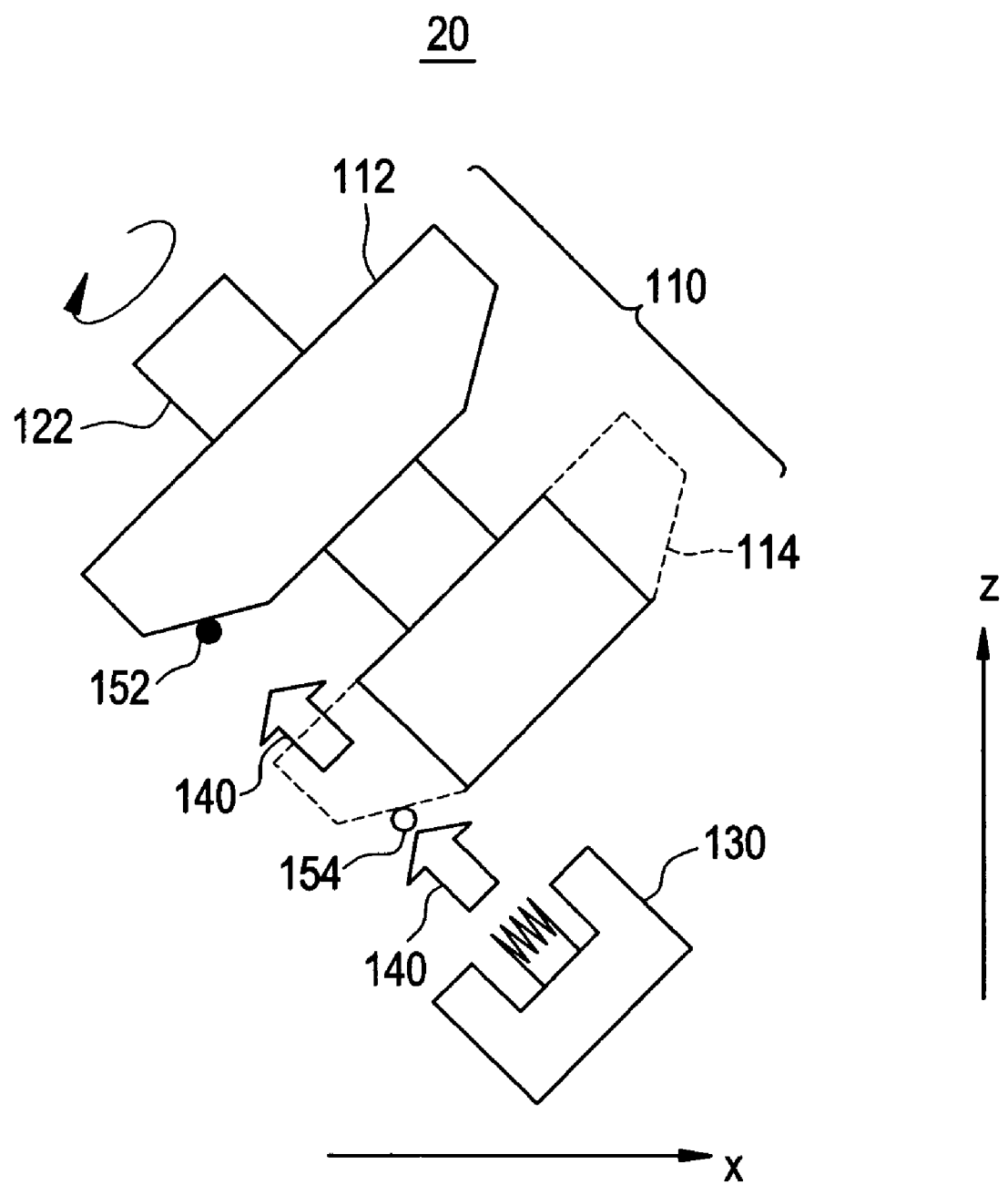
FIG. 12 is a diagram showing the location of the multiple focal points.

Focal points may be located along a direction which is aslant against the z direction and x direction. FIG. 12 shows an example of this case. The rotation shaft 122 and electron beam 140 have their direction set to be aslant against the z direction and x direction as shown in the figure. The z-x plane is the horizontal plane of the revolving coordinate system. The inclination angle is arbitrary on the z-x plane. Consequently, there is accomplished an X-ray tube 20 which generates X-rays from the two focal points 152 and 154 located along a direction which is aslant against the z direction and x direction alternately on a time-division basis. The same arrangement can be applied to the case of an X-ray tube 20 having four anodes as shown in FIG. 7 and to the case having two anodes and corresponding cathodes situated back-to-back as shown in FIG. 9.

Figure 13:
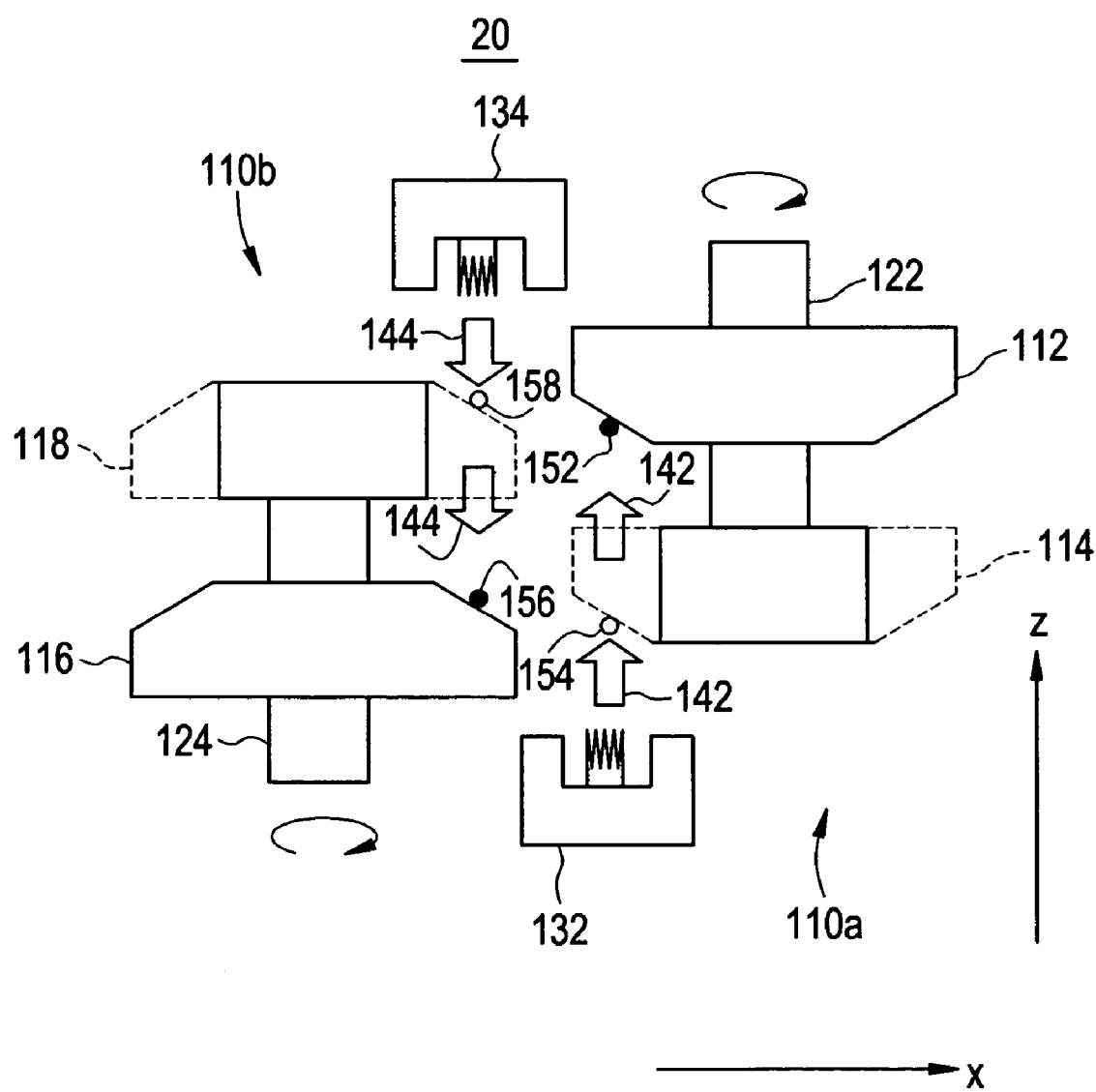
FIG. 13 is a diagram showing the location of the multiple focal points.

By having multiple pairs of anode and cathode, it is possible to make multiple focal points distributed in two-dimensional fashion on the z-x plane. FIG. 13 shows an example of this case. The X-ray tube 20 has a pair of anode 110a and cathode 132 and another pair of anode 110b and cathode 134 as shown in the figure.

The anode 110a has rotary plates 112 and 114 and a rotation shaft 122, and X-rays are generated from two focal points 152 and 154 at which an electron beam 142 from the cathode 132 impinge alternately. The anode 110b has rotary plates 116 and 118 and a rotation shaft 124, and X-rays are generated from two focal points 156 and 158 at which an electron beam 144 from the cathode 134 impinge alternately. The electron beams 142 and 144 emitted by the cathodes 132 and 134 are on the z-x plane, and therefore the focal points 152,154,156 and 158 are distributed in two-dimensional fashion on the z-x plane.

Figure 14:
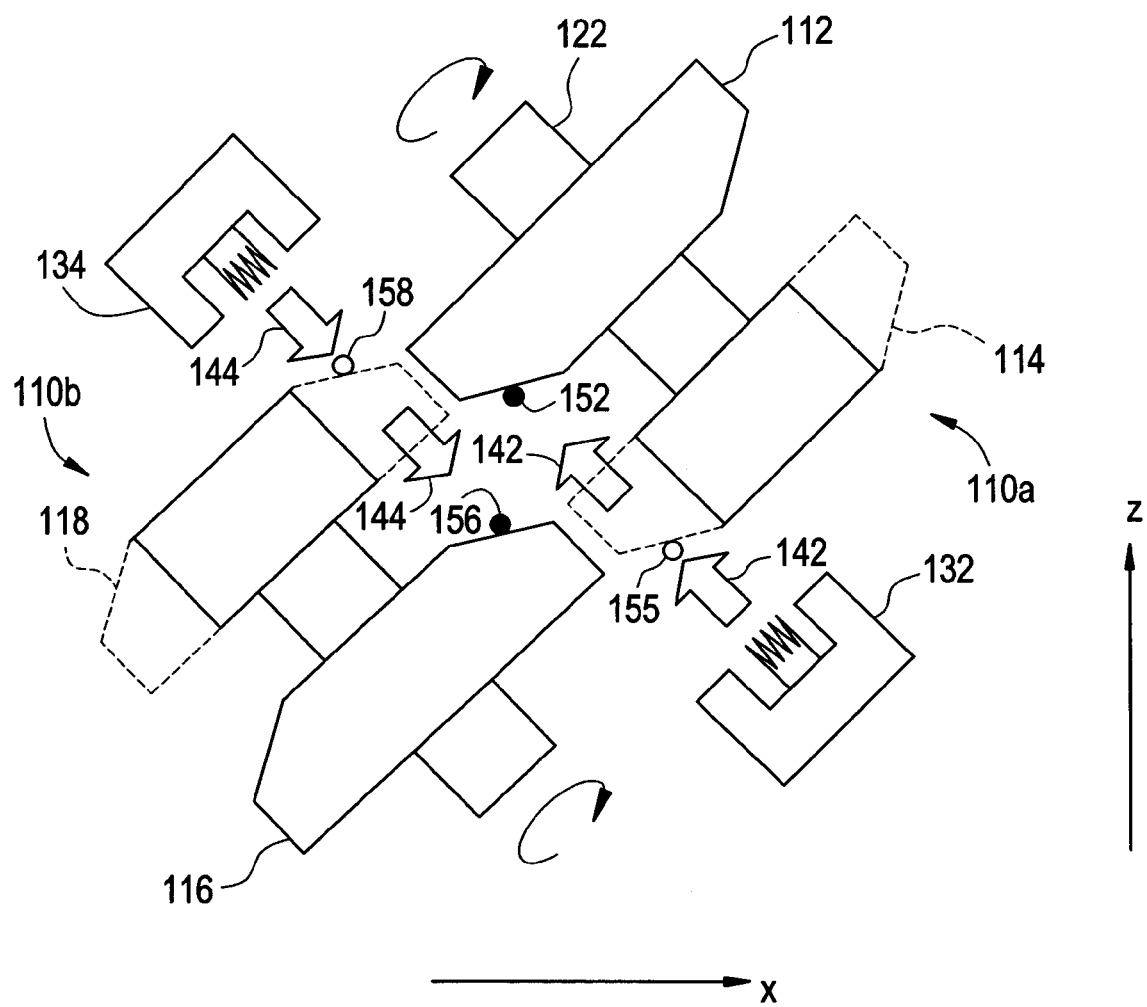
FIG. 14 is a diagram showing the location of the multiple focal points.

FIG. 14 shows another example of the distribution of four focal points on the z-x plane. The rotation shafts 122 and 124 and the electron beams 142 and 144 have their direction set to be aslant against the z direction and x direction on the z-x plane. The slanting angle is arbitrary.

In this manner, there is accomplished an X-ray tube 20 which generates X-rays sequentially on a time-division basis from four focal points 152,154,156 and 158 distributed in two-dimensional fashion on the z-x plane. The number of focal points can further be increased by including more than two pairs of anode and cathode. The anode and cathode pairs may be arranged as shown in FIG. 7 or FIG. 9.

The plane on which multiple focal points are distributed may be a plane which is aslant against the z-x plane. The focal point distribution on such a plane can be attained by arranging the anodes and cathodes such that the relation shown in FIG. 13 or FIG. 14 for example is fulfilled on the plane which is aslant against the z-x plane. Alternatively, multiple focal points may be located to have distinct three-dimensional positions, instead of being located to belong to a common plane.

Figure 15:
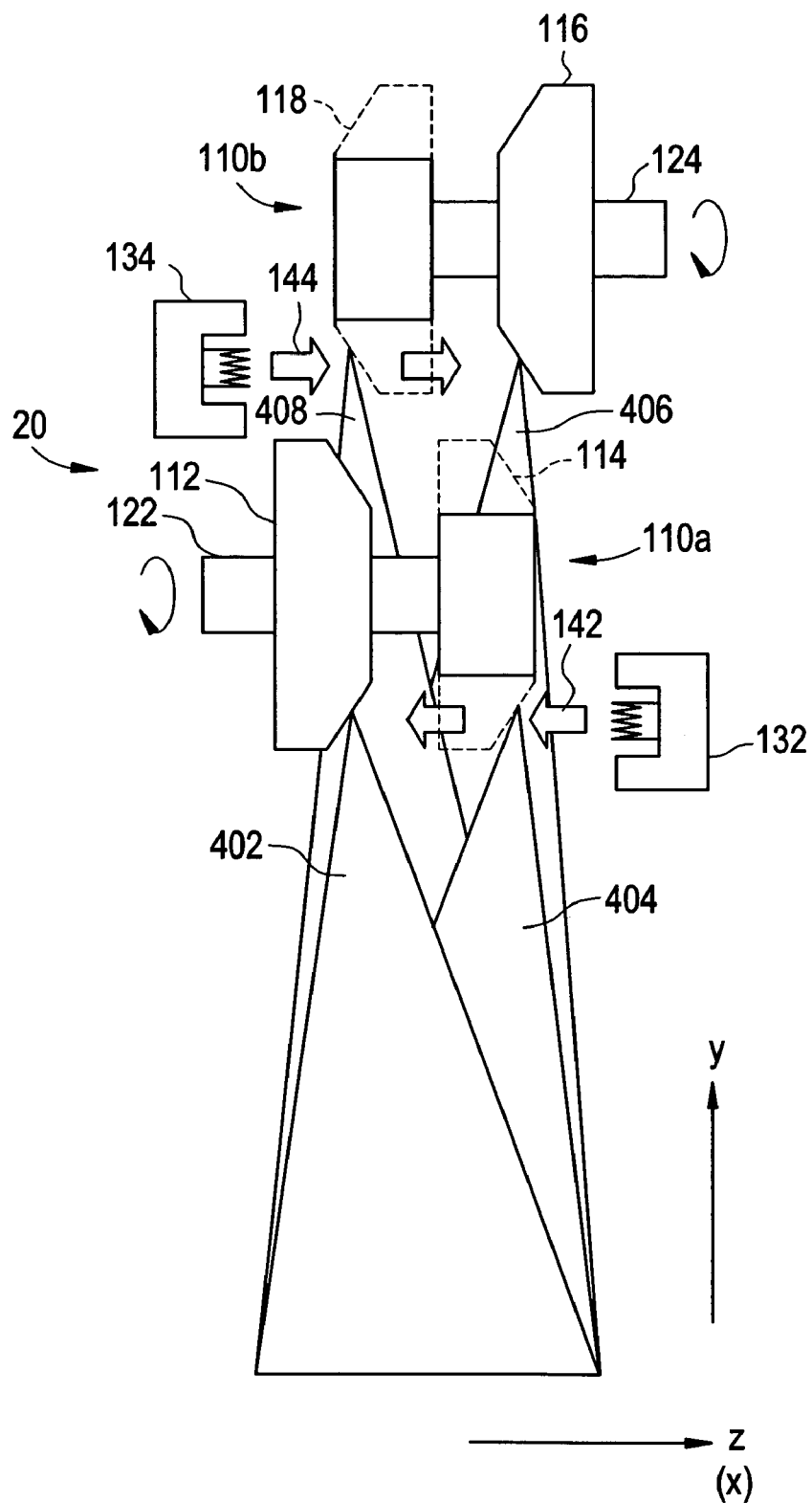
FIG. 15 is a diagram showing the arrangement of the X-ray irradiation/detection equipment.

In this case, it is possible to obtain X-rays 402,404,406 and 408 which are generated sequentially on a time-division basis from four focal points which are different in position in the z direction or x direction or a direction which is aslant against these directions and also different in position in the y direction, as shown in FIG. 15 for example. Filtering these X-rays with different filters enables the imaging based on four X-rays of different energy levels.

Figure 16:
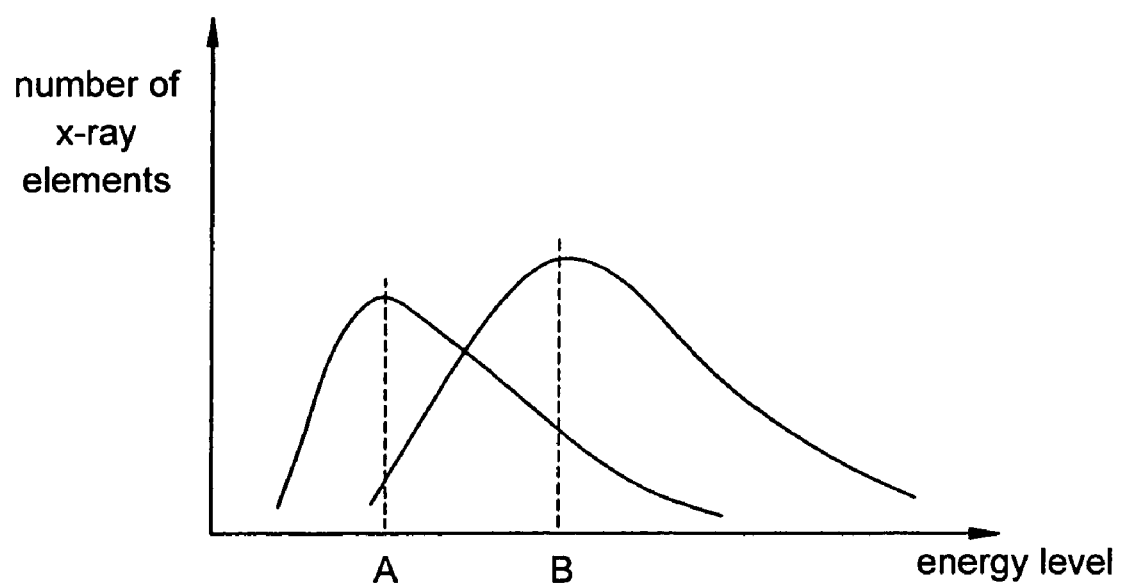
FIG. 16 is a diagram showing the characteristics of the filter.

In the case of imaging by use of two kinds of X-rays of different energy levels, two filters having selecting characteristics which correspond to the relevant effective energy levels A and B, as shown in FIG. 16 for example, are used. In FIG. 16, an energy level of a number of X-ray elements of X-rays generated by X-ray tube 20 is plotted on an a-axis and the number of X-ray elements is plotted on a v-axis. A quantitative image for intended substances is obtained by computation from an image which is reconstructed from projection data derived from the X-rays of energy level A and an image which is reconstructed from projection data derived from the X-rays of energy level B.

The CT value of the image which is reconstructed from projection data derived from the X-rays of energy level A and the CT value of the image which is reconstructed from projection data derived from the X-rays of energy level B are given by the following formulas.

$$CT_A = \alpha_A X + \beta_A Y + \gamma_A$$

$$CT_B = \alpha_B X + \beta_B Y + \gamma_B$$

In the formulas, X and Y are values (unknowns) of the intended substances. $\alpha A$, $\alpha B$, $\beta A$, $\beta B$, $\gamma A$, and $\gamma B$ are constants which are evaluated by the preliminary measurement.

The X and Y are evaluated from these CT values based on the following formulas:

$$X = \frac{(CT_A - \gamma_A)\beta_B - (CT_B - \gamma_B)\beta_A}{\alpha_A \beta_B - \alpha_B \beta_A}$$

$$Y = \frac{(CT_A - \gamma_A)\alpha_\beta - (CT_B - \gamma_B)\alpha_A}{\beta_A \alpha_B - \beta_B \alpha_A}$$

And, an image pertaining to X and an image pertaining to Y are formed. The X and Y are, for example, BMD (bone mineral density), lipid, iron, etc.

It is also possible to perform imaging at a same energy level for all X-rays, instead of energy selection with filters. In this case, X-rays generated from multiple focal points have their geometries differing slightly from each other, and therefore, images which are reconstructed from projection data derived from these X-rays are superior in spatial resolution, less artifact, and more accurate relative to images which are reconstructed from projection data derived from X-rays from one focal point.

The X-ray tube 20, which generates X-rays sequentially on a time-division basis from multiple focal points which are different in their three-dimensional positions, is suitable not only for imaging by X-rays of multiple energy levels, but also in addition for high-accuracy imaging. In case high-accuracy imaging is not required, it is also possible to use, by selecting from among multiple focal points, a focal point which provides X-rays having the best property.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An X-ray CT apparatus comprising:
an X-ray tube which generates X-rays from multiple focal points of different 3-dimensional positions sequentially on a time-division basis, wherein said X-ray tube comprises an anode and a cathode which confront each other and generate X-rays from focal points on said anode where electrons from said cathode impinge, wherein said anode has multiple impingement portions where electrons released by said cathode impinge at multiple positions on a trajectory of electrons sequentially on a time-division basis, wherein said anode comprises a plurality of rotary plates which are parallel to each other and share a rotation shaft which is parallel to the trajectory of electrons, wherein said rotary plates are located from a position nearest to said cathode up to a position immediately before a position farthest from said cathode, each of said rotary plates having large-radius sections with a radius larger than a distance from a rotation center to the trajectory of electrons and small-radius sections with a radius smaller than the distance from the rotation center to the trajectory of electrons by being formed alternately along a rotational direction such that the large-radius sections of said rotary plates do not overlap in a direction parallel to the trajectory of electrons;
a plurality of filters which implement filtering individually for the X-rays generated individually from the focal points;
a collimator which equalizes an irradiation range of the X-rays generated individually from the focal points;

a collection device which collects projection data of multiple views of a subject of imaging for the X-rays generated individually from the focal points; and a reconstruction device which reconstructs an image based on the projection data.

2. An X-ray CT apparatus according to claim 1, wherein said plurality of rotary plates includes two rotary plates.

3. An X-ray CT apparatus according to claim 1 including a plurality of pairs of said anode and cathode.

4. An X-ray CT apparatus according to claim 3 including two pairs of said anode and cathode.

5. An X-ray CT apparatus according to claim 3, wherein said focal points are all located on the same horizontal plane.

6. An X-ray CT apparatus according to claim 3, wherein said focal points are all located on a plane which is aslant against a horizontal plane.

7. An X-ray CT apparatus comprising:

an X-ray tube which generates X-rays from multiple focal points of different 3-dimensional positions sequentially on a time-division basis, wherein said X-ray tube comprises an anode and a cathode which confront each other and generate X-rays from focal points on said anode where electrons from said cathode impinge, wherein said anode has multiple impingement portions where electrons released by said cathode impinge at multiple positions on a trajectory of electrons sequentially on a time-division basis, wherein said anode comprises two rotary plates which are parallel to each other and share a rotation shaft which is parallel to the trajectory of electrons released by said cathode, said rotary plates having X-ray generation sections and X-ray non-generation sections which are laid out on surfaces of opposite sides alternately along a rotational direction such that the X-ray generation sections on the surfaces of opposite sides do not overlap in a direction parallel to the rotation shaft, and wherein said cathode generates electrons which impinge on the surfaces of opposite sides of said two rotary plates;

a plurality of filters which implement filtering individually for the X-rays generated individually from the focal points;

a collimator which equalizes an irradiation range of the X-rays generated individually from the focal points;

a collection device which collects projection data of multiple views of a subject of imaging for the X-rays generated individually from the focal points; and a reconstruction device which reconstructs an image based on the projection data.

8. An X-ray CT apparatus according to claim 7 including a plurality of pairs of said anode and cathode.

9. An X-ray CT apparatus according to claim 8 including two pairs of said anode and cathode.

10. An X-ray CT apparatus according to claim 8, wherein said focal points are all located on the same horizontal plane.

11. An X-ray CT apparatus according to claim 8, wherein said focal points are all located on a plane which is aslant against a horizontal plane.

12. An X-ray tube including an anode and a cathode which confront each other and generating X-rays from focal points on said anode where electrons from said cathode impinge, said anode having multiple impingement portions where electrons released by said cathode impinge at multiple positions on the trajectory of electrons sequentially on a time-division basis, wherein said anode comprises a plurality of rotary plates which are parallel to each other and share a rotation shaft which is parallel to a trajectory of electrons, wherein said rotary plates are located from a position nearest to said cathode up to a position immediately before a position farthest from said cathode, wherein each of said rotary plates have large-radius sections with a radius larger than a distance from a rotation center to the trajectory of electrons and small-radius sections with a radius smaller than the distance from the rotation center to the trajectory of electrons by being formed alternately along a rotational direction such that the large-radius sections of said rotary plates do not overlap in a direction parallel to the trajectory of electrons.

13. An X-ray tube according to claim 12, wherein said plurality of rotary plates includes two rotary plates.

14. An X-ray tube according to claim 12 including a plurality of pairs of said anode and cathode.

15. An X-ray tube according to claim 14 including two pairs of said anode and cathode.

16. An X-ray tube according to claim 14, wherein said focal points are all located on the same horizontal plane.

17. An X-ray tube according to claim 14, wherein said focal points are all located on a plane which is aslant against a horizontal plane.

* * * * *